United States Patent [19]

Sano

[11] Patent Number: 5,237,350
[45] Date of Patent: Aug. 17, 1993

[54] OPHTHALMIC PHOTOGRAPHIC APPARATUS USING A FLUORESCENT AGENT

[75] Inventor: Eiichi Sano, Tokyo, Japan

[73] Assignee: Kabushiki Kaisha Topcon, Tokyo, Japan

[21] Appl. No.: 764,281

[22] Filed: Sep. 23, 1991

[30] Foreign Application Priority Data

Sep. 25, 1990 [JP] Japan .................. 2-254555

[51] Int. Cl.$^5$ .............................. A61B 3/10
[52] U.S. Cl. .................... 351/213; 351/206; 351/233; 354/62
[58] Field of Search ............... 351/206, 207, 213, 233; 354/62

[56] References Cited

U.S. PATENT DOCUMENTS 4,799,783  1/1989  Takahashi et al. .............. 351/206
5,118,179  6/1992  Sano et al. ..................... 351/206
5,152,295 10/1992  Kobayashi et al. ............. 351/206

Primary Examiner—Rodney B. Bovernick
Assistant Examiner—Hung Xuan Dang
Attorney, Agent, or Firm—Finnegan, Henderson, Farabow, Garrett & Dunner

[57] ABSTRACT

The ophthalmic photographic apparatus of the invention comprises a means of detecting abnormalities in the filters used when a fluorescent agent is caused to fluoresce by infra-red light in order to photograph a subject's eye. According to the ophthalmic photographic apparatus of the invention, the abnormality-detecting means detects an abnormality if there is a flaw or deterioration of a filter used to take a photograph when a fluorescent agent is caused to fluoresce by infra-red light. The abnormality-detecting means preferably detects abnormalities of an exciter filter which transmits infra-red light in a specific wavelength range which causes fluorescence of a fluorescent agent in an illuminating optical system having an illuminating light source. More specifically, this abnormality-detecting means comprises a reflecting mirror, disposed on the opposite side of the exciter filter to the illuminating light source, which reflects a part of the illuminating light (here, the term illuminating light will be understood to mean infra-red light in the specific wavelength range and illuminating light in other wavelength ranges) that has passed through the exciter filter; a photodetector disposed in the direction of reflection of the reflecting mirror which detects illuminating light reflected by the mirror; and a discriminating circuit which determines whether or not there is an abnormality in the exciter filter according to the output variation of the photodetector.

5 Claims, 3 Drawing Sheets

OPHTHALMIC PHOTOGRAPHIC APPARATUS USING A FLUORESCENT AGENT

BACKGROUND OF THE INVENTION

1. Field of the Invention

This invention concerns the improvement of an ophthalmic photographic apparatus such as a fundus camera for photographing the fundus of a subject's eye using a fluorescent agent.

2. Description of the Prior Art

An ophthalmic photographic apparatus is well known in the prior art wherein the method of use consists of intraveneously injecting the fluorescent agent fluorescein, illuminating a fundus of a subject's eye with light in the visible wavelength region to cause the fluorescent agent to fluoresce, and photographing the fundus by means of the fluorescence emitted by the fluorescent agent.

In recent years, a fundus camera has been developed wherein the method of use consists of intravenously injecting the fluorescent agent indocyanin green, illuminating the fundus by light in the infra-red region to cause the fluorescent agent to fluoresce, and photographing the fundus. In this fundus camera wherein the method of use consists of illuminating the fundus by light in the infra-red region, an exciter filter which transmits only infra-red light in a specific wavelength range that causes the fluorescent agent to fluoresce is inserted in the illuminating optical system when the photograph is taken. And a barrier filter is inserted in a photographic optical system when the photograph is taken.

In order to cause the fluorescent agent to fluoresce by illuminating the fundus with infra-red light, however, an intense illumination is required. If there should thus happen to be a flaw or deterioration of the exciter filter provided in the illuminating optical system, not only infra-red light in the specific wavelength range but also light in other wavelength ranges reaches the fundus, and may cause damage to the retina of the subject's eye. Further, if there should happen to be a flaw or deterioration of the barrier filter which is provided in the photographic optical system, infra-red light in the specific wavelength range passes through the barrier filter in addition to the fluorescence of the fluorescent agent so as to form an image. The photographic image is therefore blurred, and a good photograph cannot be obtained.

SUMMARY OF THE INVENTION

It is therefore an object of the present invention to provide an ophthalmic photographic apparatus for detecting abnormalities in filters when a photograph is taken by causing a fluorescent agent to fluoresce under illumination with infra-red light in a specific wavelength range.

To achieve the aforesaid object, the ophthalmic photographic apparatus of the invention comprises means for detecting abnormalities in the filter used when a fluorescent agent is caused to fluoresce by infra-red light in order to photograph a subject's eye.

According to the ophthalmic photographic apparatus of the present invention, the aforesaid abnormality-detecting means detects an abnormality if there is a flaw or deterioration of a filter used to take a photograph when a fluorescent agent is caused to fluoresce by infra-red light.

The abnormality-detecting means preferably detects an abnormality in an exciter filter which transmits infra-red light in a specific wavelength range that causes fluorescence of a fluorescent agent in an illuminating optical system having an illuminating light source.

More specifically, this abnormality-detecting means comprises a reflecting mirror which reflects part of the illuminating light (here, the term illuminating light will be understood to mean infra-red light in the specific wavelength range and illuminating light in other wavelength ranges) that has passed through an exciter filter disposed on the opposite side of the filter to an illuminating light source; a photodetector disposed in the direction of reflection of the reflecting mirror which detects illuminating light reflected by the reflecting mirror; and a discriminating circuit which determines whether or not there is an abnormality in the exciter filter according to the output variation of the photodetector.

This reflecting mirror is preferably a dichroic mirror which transmits infra-red light in the specific wavelength range and reflects illuminating light of other wavelengths. In this case, therefore, even if for example there is an abnormality in the exciter filter, illuminating light of wavelengths other than infra-red light in the specific wavelength range is completely prevented from reaching the subject's eye and causing damage to it.

DESCRIPTION OF THE PREFERRED EMBODIMENTS

Figure 1:
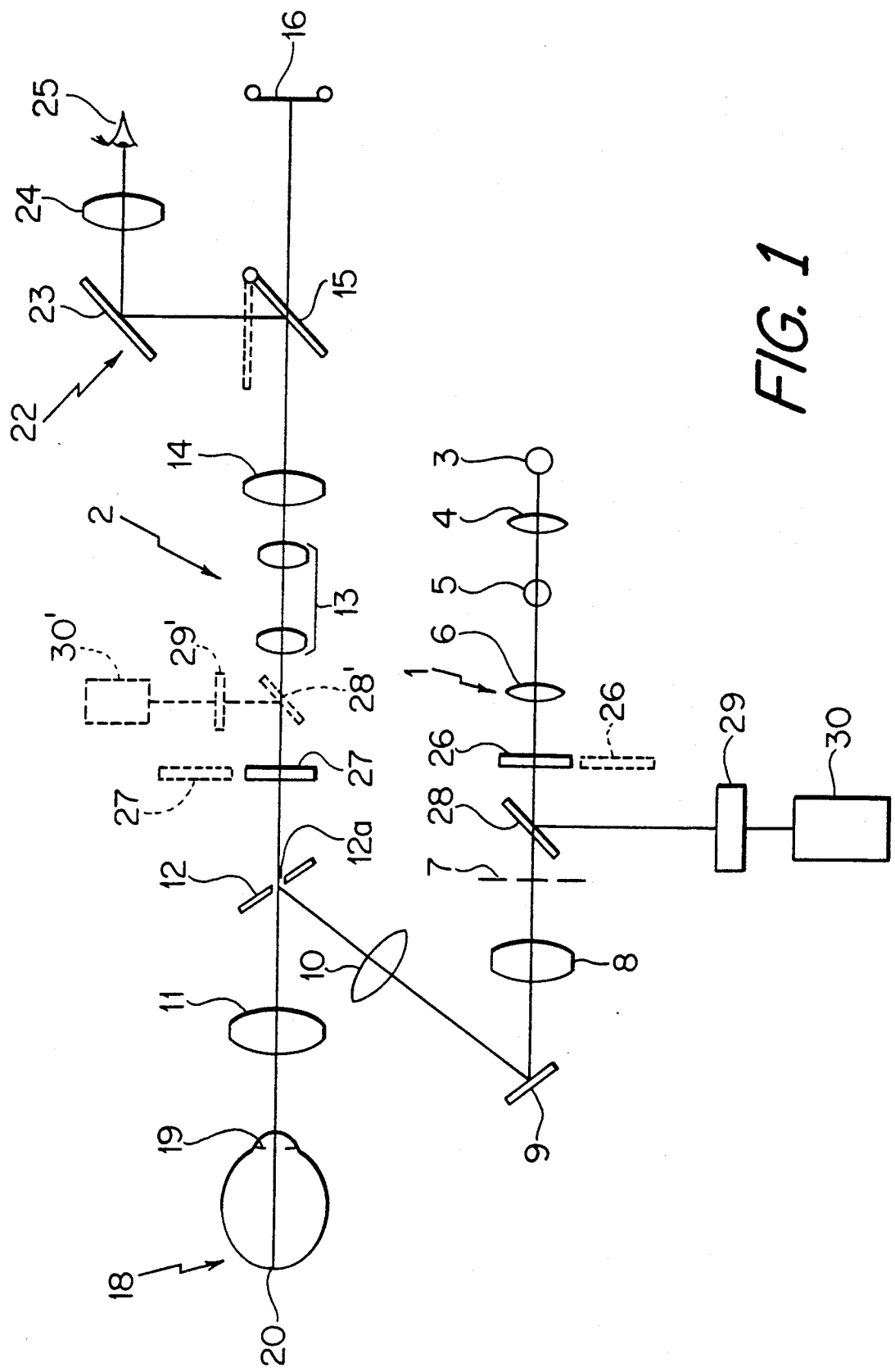
FIG. 1 is an optical drawing illustrating a first embodiment of an ophthalmic photographic apparatus according to the present invention.

FIG. 1 illustrates a first embodiment of an ophthalmic photographic apparatus according to the present invention. In the FIG., 1 is an illuminating optical system, and 2 is a photographic optical system. The illuminating optical system 1 essentially comprises a halogen lamp 3 as an illuminating light source for making observations, a condenser lens 4, a xenon lamp 5 as an illuminating light source for taking photographs, a condenser lens 6, a ring-shaped diaphragm 7, a relay lens 8, a full reflecting mirror 9 and a relay lens 10.

The photographic optical system 2 comprises an objective lens 11, a holed mirror 12, focussing lenses 13, an image-forming lens 14, a quick return mirror 15 and a film 16. The objective lens 11 is adjacent to the subject's eye 18. The ring-shaped diaphragm 7 is in an approximately conjugate position to the pupil of the subject's eye 18 with respect to the relay lenses 8 and 10, and the objective lens 11.

When making observations, illuminating light from the halogen lamp 3 is brought to the subject's eye 18 via the condensing lenses 4 and 6, the ring-shaped diaphragm 7, the relay lens 8, the full reflecting mirror 9, the relay lens 10, the holed mirror 12 and the objective lens 11, and thereby illuminates the fundus 20 of the subject's eye 18. This illuminating light is ring-shaped when it passes through the pupil 19 of the subject's eye 18.

The light beam from the fundus 20 is brought to the holed mirror 12 via the objective lens 11, and reaches the quick return mirror 15 via the hole 12a, the focussing lenses 13 and the image-forming lens 14. The quick return mirror 15 is inserted in the optical path of the photographic optical system 2 when making observations. The light beam from the fundus 20 is reflected by this quick return mirror, and enters an observer's eye 25 via a mirror 23 and eyepiece 24 of an eyepiece optical system 22. The fundus 20 of the subject's eye 18 may then be observed.

Figure 2:
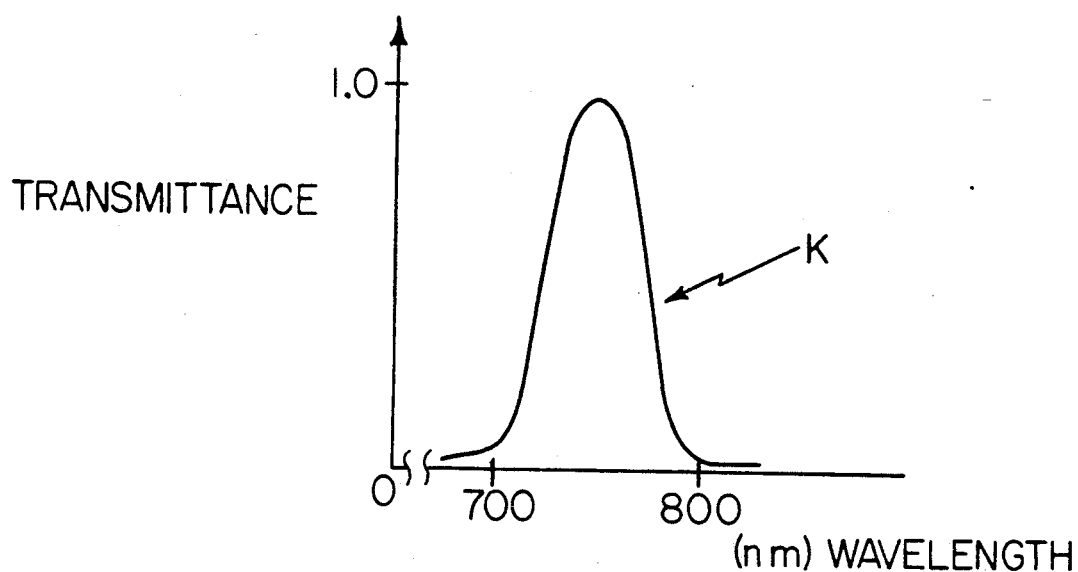
FIG. 2 is a drawing illustrating the transmittance characteristics of the exciter filter for transmitting infra-red light in a specific wavelength range shown in FIG. 1.
Figure 3:
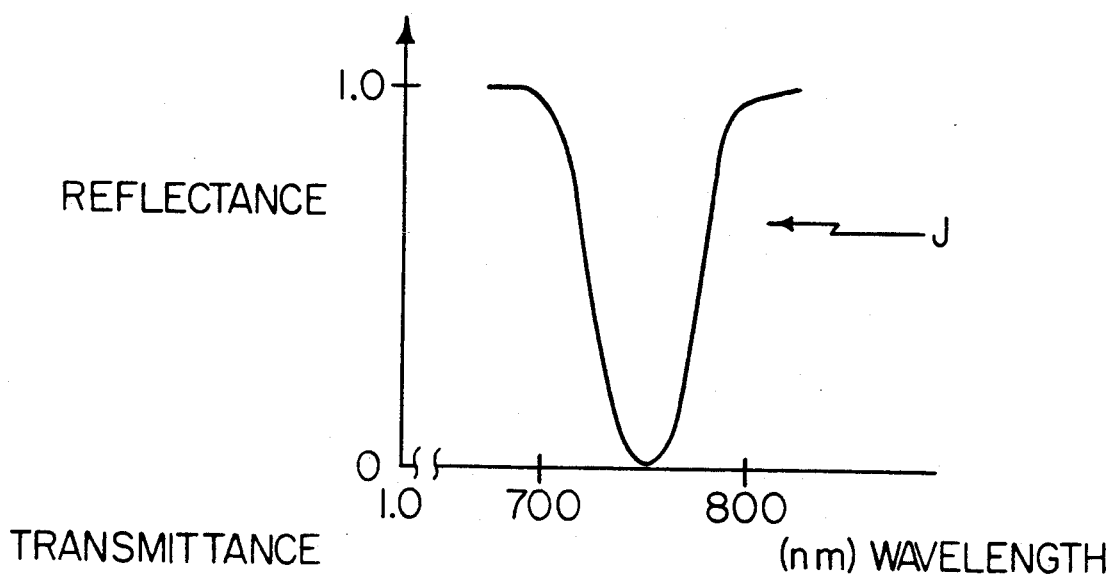
FIG. 3 is a drawing illustrating the reflectance characteristics of the dichroic mirror shown in FIG. 1.

When taking photographs by means of infra-red illuminating light, an exciter filter 26 which transmits infra-red light in a specific wavelength range is inserted in the optical path between the ring-shaped diaphragm 7 and the condenser lens 6 of the illuminating optical system 1. Further, a barrier filter 27 is inserted between the holed mirror 12 and the focussing lenses 13 of the photographic optical system 2. The exciter filter 26 has a transmittance characteristic K that transmits infra-red light in the specific wavelength range between 700 nm and 800 nm as shown in FIG. 2. The barrier filter 27 performs the function of transmitting fluorescence which has a infra-red wavelength caused by infra-red light in the specific wavelength range, and cutting out infra-red light in this range. When taking photographs, a reflecting mirror 28 is inserted in the illuminating optical system 1 on the opposite side of the exciter filter 26 to the xenon lamp 5 between the ring-shaped diaphragm 7 and the exciter filter 26. In this embodiment, the reflecting mirror 28 is a dichroic mirror. This reflecting mirror 28 has a wavelength characteristic J that reflects illuminating light of wavelength below 700 nm or above 800 nm, and transmits infra-red light in the specific wavelength range between 700 nm and 800 nm. A photodetector 29 is disposed in the direction of reflection of the reflecting mirror 28 which detects the light reflected by the mirror. The output of this photodetector 29 is input to a discriminating circuit 30. The discriminating circuit 30, the reflecting mirror 28 and the photodetector 29 function as an abnormality-detecting means which detects abnormalities such as a flaw or deterioration of the exciter filter 26.

When taking photographs under infra-red illumination, the xenon lamp 5 is switched on by a shutter switch, not shown. The fundus 20 is thereby illuminated, the quick return mirror 15 is simultaneously removed from the optical path of the photographic optical system 2, and fluorescent light from the fundus 20 is brought to the film 16.

If there happens to be a flaw or deterioration of the exciter filter 26, illuminating light of wavelengths below 700 nm and above 800 nm is brought via the filter 26 to the reflecting mirror 28 as well as infra-red light in the specific wavelength range. The reflecting mirror 28 however has the property of reflecting illuminating light of wavelengths below 700 nm and above 800 nm, so that even if there is a flaw or deterioration of the exciter filter 26, the fundus 20 does not suffer any damage. At the same time, if there is such a flaw or deterioration of the exciter filter 26, the photodetector 29 detects illuminating light of wavelengths below 700 nm and above 800 nm, and its output varies depending on the light amount variation and the wavelength variation. The discriminating circuit 30 determines whether or not there is an abnormality such as a flaw or deterioration of the exciter filter 26 based on this output variation of the photodetector.

Figure 4:
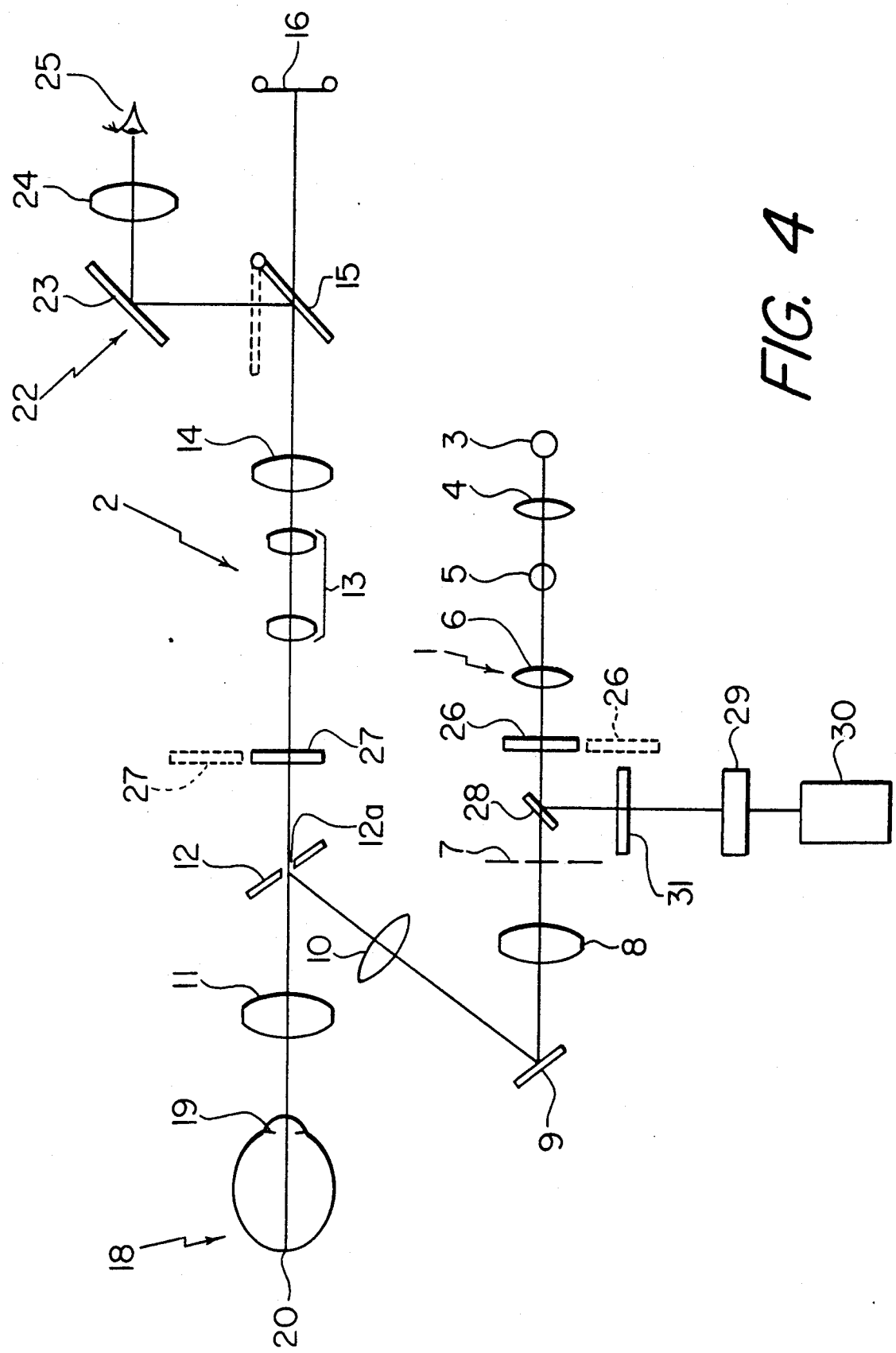
FIG. 4 is an optical drawing illustrating a second embodiment of an ophthalmic photographic apparatus according to the present invention.

FIG. 4 illustrates a second embodiment of an ophthalmic photographic apparatus according to the present invention. In this embodiment, the reflecting mirror 28 is a half mirror instead of a dichroic mirror. In the case of this second embodiment, a minus filter 31 with inverse wavelength characteristics to those of the exciter filter 26, is provided between the reflecting mirror 28 and the photodetector 30. In other words, the minus filter 31 performs the function of reflecting infra-red light of wavelengths from 700 nm to 800 nm, and transmitting illuminating light in other wavelength ranges. In this case, a reflecting mirror 28 with a small reflecting surface is chosen so that it does not obstruct infra-red light in the specific wavelength range.

In the aforesaid embodiments, the arrangement is designed to detect an abnormality such as a flaw or deterioration of the exciter filter 26, but it may also be designed to detect an abnormality such as a flaw or deterioration of the barrier filter 27 by providing a reflecting mirror 28' between the focussing lenses 13 and the barrier filter, performing detection with a photodetector 29', and performing determination with a discriminating circuit 30'.

What is claimed is:

1. An ophthalmic photographic apparatus having an exciter filter which transmits infra-red light in a specific wavelength range in order to cause a fluorescent agent to fluoresce, this filter being disposed in an illuminating optical system having an illuminating light source which illuminates a subject's eye, and an abnormality-detecting means which detects abnormalities in said exciter filter, said abnormality-detecting means comprises a reflecting mirror, disposed on the opposite side of said exciter filter to the illuminating light source, which reflects a part of the illuminating light that has passed through said exciter filter; a photodetector, disposed in the direction of reflection of said reflecting mirror, which detects illuminating light reflected by the mirror; and a discriminating circuit which determines whether or not there is an abnormality in said exciter filter according to the output variation of said photodetector.

2. An ophthalmic photographic apparatus as defined in claim 1 characterized in that a minus filter having inverse wavelength characteristics to those of said exciter filter is disposed between said reflecting mirror and said photodetector.

3. An ophthalmic photographic apparatus as defined in claim 1 characterized in that said reflecting mirror is a dichroic mirror which reflects illuminating light except infra-red light in the specific wavelength range.

4. An ophthalmic photographic apparatus as defined in claim 1 characterized in that said discriminating circuit determines whether or not there is an abnormality in said exciter filter based on a light amount variation.

5. An ophthalmic photographic apparatus as defined in claim 1 characterized in that said discriminating circuit determines whether or not there is an abnormality in said exciter filter based on a wavelength variation.

* * * * *